US010751063B2

(12) United States Patent
Hasan et al.

(10) Patent No.: US 10,751,063 B2
(45) Date of Patent: Aug. 25, 2020

(54) SHAPE MEMORY POLYMER NANOCOMPOSITES AND USES THEREOF

(71) Applicants: The Texas A&M University System, College Station, TX (US); Lawrence Livermore National Security, LLC, Livermore, CA (US)

(72) Inventors: Sayyeda Marziya Hasan, College Station, TX (US); Jennifer Nicole Rodriguez, Fremont, CA (US); Pooja Singhal, Redwood City, CA (US); Thomas Stephen Wilson, San Leandro, CA (US); Duncan J. Maitland, College Station, TX (US)

(73) Assignees: Lawrence Livermore National Security, LLC, Livermore, CA (US); The Texas A&M University Systsem, College Station, TX (US)

( * ) Notice: Subject to any disclaimer, the term of this patent is extended or adjusted under 35 U.S.C. 154(b) by 81 days.

(21) Appl. No.: 15/575,896

(22) PCT Filed: May 25, 2016

(86) PCT No.: PCT/US2016/034160
§ 371 (c)(1),
(2) Date: Nov. 21, 2017

(87) PCT Pub. No.: WO2016/191492
PCT Pub. Date: Dec. 1, 2016

(65) Prior Publication Data
US 2018/0140304 A1 May 24, 2018

Related U.S. Application Data

(60) Provisional application No. 62/166,652, filed on May 26, 2015.

(51) Int. Cl.
*A61B 17/12* (2006.01)
*A61L 31/12* (2006.01)
(Continued)

(52) U.S. Cl.
CPC .. *A61B 17/12113* (2013.01); *A61B 17/12131* (2013.01); *A61L 31/128* (2013.01); *A61L 31/14* (2013.01); *A61L 31/146* (2013.01); *A61L 31/18* (2013.01); *A61B 17/1219* (2013.01); *A61B 2017/00526* (2013.01);
(Continued)

(58) Field of Classification Search
CPC ...................................... A61B 17/12
See application file for complete search history.

(56) References Cited

U.S. PATENT DOCUMENTS

| 2002/0022672 A1 | 2/2002 | Thunhorst et al. |
| 2010/0184901 A1 | 7/2010 | Adochio et al. |
| 2012/0158034 A1 | 6/2012 | Wilson et al. |

OTHER PUBLICATIONS

International Searching Authority, "Notification of Transmittal of the International Search Report and the Written Opinion of the International Searching Authority," dated Aug. 31, 2016, in International application No. PCT/US2016/034160.
(Continued)

*Primary Examiner* — Matthew W Schall
(74) *Attorney, Agent, or Firm* — Trop, Pruner & Hu, P.C.

(57) ABSTRACT

The invention relates to radiopaque shape memory foam compositions and methods of using the compositions. In certain embodiments, the compositions are used in neurovascular occlusion applications.

14 Claims, 8 Drawing Sheets

(a)

(b)

(d)

(c)

(51) Int. Cl.
*A61L 31/14* (2006.01)
*A61L 31/18* (2006.01)
*A61M 31/00* (2006.01)
*A61B 17/00* (2006.01)
*A61B 90/00* (2016.01)

(52) U.S. Cl.
CPC ........... *A61B 2017/00871* (2013.01); *A61B 2090/3966* (2016.02); *A61L 2400/12* (2013.01); *A61L 2400/16* (2013.01); *A61M 31/002* (2013.01); *C08L 2201/12* (2013.01)

(56) References Cited

OTHER PUBLICATIONS

Rodriguez, et al., Opacification of Shape Memory Polymer Foam Designed for Treatment of Intracranial Anaurysms, NIH Public Access, Ann. Biomed. Eng., vol. 40(4), Apr. 2012, pp. 883-897.
Hasan, et al., Tungsten-Loaded SMP foam nanocomposities with inherent radioacity and tunable thermo-mechanical properties, Polym. Adv. Technol., vol. 27, Aug. 11, 2015, pp. 195-203.
Hasan, et al., "Effects of Isophorone Diisocyanate on the Thermal and Mechanical Properties of Shape-Memory Polyurethane Foams", Macromolecular Chemistry and Physics, Macromolecular Journal, 2014, 10 pages.
Hasan, et al., "Modification of shape memory polymer foams using tungsten, aluminum oxide, and silicon dioxide nanoparticles", RSC Advances, Royal Society of Chemistry 2016, Dec. 18, 2015, pp. 918-927.

Composition of foams using 100% trimethylhexamethylene diisocyanate (TMHDI) for the isocyanate component of the urethane foam and increasing volume percent concentration of W nanoparticles. Three foam batches were synthesized and the average weight percent of the monomers and volume percent of tungsten nanoparticles was determined for all batches.

| Composition | W (vol %) | TMHDI (wt %) | HPED (wt %) | TEA (wt %) | Water (wt %) | T-131 (wt %) | BL-22 (wt %) | DC 198 (wt %) | DC 5943 (wt %) | Enzyme (PPH) |
|---|---|---|---|---|---|---|---|---|---|---|
| 100 TMDHI 0% W | 0.00 ±0 | 66.70 ±0.1 | 17.11 ±0.02 | 5.74 ±0.01 | 2.35 ±0 | 0.26 ±0 | 0.65 ±0 | 2.62 ±0.1 | 4.59 ±0.01 | 14.88 ±0 |
| 100 TMDHI 4% W | 4.00 ±0.001 | 66.72 ±0.03 | 17.10 ±0.04 | 5.75 ±0.03 | 2.35 ±0.01 | 0.26 ±0.01 | 0.65 ±0.01 | 2.71 ±1 | 5.45 ±1 | 14.57 ±2 |
| 100 TMHDI 5% W | 4.99 ±0.002 | 66.69 ±0.01 | 17.13 ±0.02 | 5.74 ±0 | 2.36 ±0 | 0.26 ±0 | 0.65 ±0 | 2.56 ±0.03 | 4.61 ±0.1 | 14.55 ±2 |
| 100 TMHDI 6% W | 5.99 ±0.01 | 66.72 ±0.04 | 17.12 ±0.02 | 5.74 ±0 | 2.35 ±0 | 0.26 ±0 | 0.66 ±0.01 | 2.55 ±0.02 | 4.60 ±0.04 | 14.55 ±2 |
| 100 TMHDI 7% W | 6.99 ±0.01 | 66.75 ±0.04 | 17.12 ±0.02 | 5.74 ±0 | 2.34 ±0.01 | 0.26 ±0.01 | 0.65 ±0.01 | 2.54 ±0.02 | 4.60 ±0.03 | 17.00 ±0.1 |
| 100 TMHDI 8% W | 7.98 ±0.01 | 66.71 ±0.1 | 17.13 ±0.03 | 5.74 ±0.03 | 2.35 ±0.01 | 0.26 ±0.01 | 0.65 ±0.01 | 2.54 ±0.02 | 4.61 ±0.01 | 16.98 ±0.04 |
| 100 TMHDI 9% W | 8.98 ±0.01 | 66.76 ±0.1 | 17.12 ±0 | 5.74 ±0.03 | 2.35 ±0.01 | 0.26 ±0 | 0.64 ±0 | 2.56 ±0 | 4.58 ±0.02 | 17.00 ±0.04 |
| 100 TMHDI 10% W | 9.98 ±0.01 | 66.73 ±0.1 | 17.13 ±0 | 5.74 ±0.02 | 2.35 ±0.01 | 0.26 ±0 | 0.64 ±0 | 2.55 ±0.02 | 4.61 ±0.02 | 16.99 ±0.04 |
| 100 TMHDI 11% W | 10.97 ±0.01 | 66.72 ±0.03 | 17.11 ±0 | 5.74 | 2.36 ±0.01 | 0.25 ±0 | 0.65 | 2.60 ±0.01 | 4.58 ±0.02 | 17.00 ±0.02 |

Figure 1

Key physical and thermal properties of the SMP foam nanocomposites.

| W (vol %) | $\rho_{foam}$ (g·cm$^{-3}$) | $\rho_{net}$ (g·cm$^{-3}$) | Porosity (%) | Dry $T_g$ (°C) | Wet $T_g$ (°C) | Volume Recovery (%) | Volume Expansion (x) |
|---|---|---|---|---|---|---|---|
| 0% W | 0.013 ± 0.001 | 1.0 ± 0.02 | 99 ± 0.1 | 58 ± 2 | 34 ± 1 | 108 ± 24 | 63 ± 14 |
| 4% W | 0.033 ± 0.004 | 1.8 ± 0.03 | 98 ± 0.2 | 63 ± 1 | 28 ± 1 | 82 ± 15 | 21 ± 4 |
| 5% W | 0.041 ± 0.000 | 2.0 ± 0.04 | 98 ± 0.0 | 65 ± 1 | 35 ± 0 | 99 ± 19 | 29 ± 11 |
| 6% W | 0.045 ± 0.002 | 2.2 ± 0.04 | 98 ± 0.1 | 67 ± 0 | 38 ± 1 | 93 ± 17 | 41 ± 8 |
| 7% W | 0.045 ± 0.004 | 2.4 ± 0.05 | 98 ± 0.2 | 66 ± 1 | 39 ± 1 | 94 ± 19 | 36 ± 11 |
| 8% W | 0.054 ± 0.009 | 2.6 ± 0.05 | 98 ± 0.4 | 67 ± 1 | 41 ± 0 | 99 ± 13 | 35 ± 7 |
| 9% W | 0.060 ± 0.011 | 2.8 ± 0.06 | 98 ± 0.4 | 66 ± 1 | 41 ± 1 | 105 ± 17 | 32 ± 10 |
| 10% W | 0.048 ± 0.003 | 3.0 ± 0.06 | 98 ± 0.1 | 68 ± 1 | 41 ± 1 | 98 ± 16 | 36 ± 10 |

Figure 2

Key mechanical properties of the SMP foam nanocomposites.

| W (vol %) | Modulus (kPa) | Ultimate Tensile Strength (kPa) | Toughness (J·m⁻³) | Strain at Break (%) |
|---|---|---|---|---|
| 0% W | 2598 ± 197 | 96 ± 23 | 97 ± 29 | 20 ± 1 |
| 4% W | 10103 ± 439 | 117 ± 16 | 46 ± 7 | 9 ± 1 |
| 5% W | 6293 ± 415 | 107 ± 18 | 60 ± 12 | 12 ± 0 |
| 6% W | 5698 ± 1107 | 90 ± 5 | 48 ± 10 | 10 ± 4 |
| 7% W | 3098 ± 258 | 78 ± 3 | 40 ± 6 | 11 ± 1 |
| 8% W | 5472 ± 1909 | 82 ± 27 | 26 ± 9 | 7 ± 0 |
| 9% W | 2495 ± 1037 | 60 ± 6 | 27 ± 9 | 11 ± 2 |
| 10% W | 4075 ± 1567 | 67 ± 12 | 20 ± 13 | 9 ± 2 |

Figure 3

SHAPE MEMORY POLYMER NANOCOMPOSITES AND USES THEREOF

PRIORITY CLAIM

This application claims priority to U.S. Provisional Patent Application No. 62/166,652 filed on May 26, 2015 and entitled "SHAPE MEMORY POLYMER NANOCOMPOSITES AND USES THEREOF", the content of which is hereby incorporated by reference.

STATEMENT REGARDING FEDERALLY SPONSORED RESEARCH OR DEVELOPMENT

This invention was made with Government support under grant no. R01EB000462 awarded by the National Institute of Health National Institute of Biomedical imaging and Bioengineering. The Government has certain rights in the invention. The United States Government has rights in this application pursuant to Contract No. DE-AC52-07NA27344 between the United States Department of Energy and Lawrence Livermore National Security, LLC for the operation of Lawrence Livermore National Laboratory.

TECHNICAL FIELD

Embodiments of the invention relate to radiopaque shape memory foam compositions and methods of using the compositions. In certain embodiments, the compositions are used in neurovascular occlusion applications.

BACKGROUND OF THE INVENTION

Polymers have been utilized as medical implants for the last 30 years with much success. Some natural and synthetic polymers are known to be biocompatible, indicating their ability to perform with appropriate host response for biomedical applications. These biocompatible polymers, commonly referred to as polymeric biomaterials, are known to have a wide range of applications due to their wide availability, ease of manufacturing, and tunable mechanical and thermal properties. Some of the most common biomaterials include polyethylene (PE), polyurethane (PU), polytetrafluoroethylene (PTFE), polymethylmethacrylate (PMMA), poly (lactic acid) (PLA), and poly (glycolic acid) (PGA), which currently have found uses as biodegradable sutures and fixation screws. While these materials can be fabricated into complex shapes and are available in a wide range of compositions, most tend to have low tensile strength and Young's modulus for applications that require mechanical robustness. Additionally, polymers have similar properties to that of soft tissue, limiting their radiological detectability. Most polymeric materials lack radio-opacity because their elements possess low electron density and low specific gravity. Several steps have been taken to improve radio-opacity of polymers by incorporating heavy-metal fillers as physical mixtures, attaching heavy-metal salts to the polymer backbone via chelation, and by covalently binding radiopaque elements to monomers prior to their polymerization.

Thermally actuated shape memory polymers (SMPs) are a special class of materials that are capable of switching between a primary and a secondary shape upon a heat stimulus. These versatile materials are used for a wide range of applications such as biomaterials, textiles, and automotive. Previously synthesized SMP foams have proven to rapidly occlude aortic aneurysms and the resulting clot is stable up to 90 days. These SMP foams can further be utilized for a neurovascular occlusion device due to their ultra-low density, which allows for the material to be crimped to a small geometry and delivered to the aneurysm via catheter.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 1 includes a table showing a composition of foams using 100% trimethylhexamethylene diisocyanate (TMHDI) for the isocyanate component of the urethane foam and increasing volume percent concentration of W nanoparticles. Three foam batches were synthesized and the average weight percent of the monomers and volume percent of tungsten nanoparticles was determined for all batches.

FIG. 2 includes a table showing key physical and thermal properties of the SMP foam nanocomposites.

FIG. 3 includes a table showing key mechanical properties of the SMP foam nanocomposites.

DETAILED DESCRIPTION OF EXEMPLARY EMBODIMENTS

Figure 4:
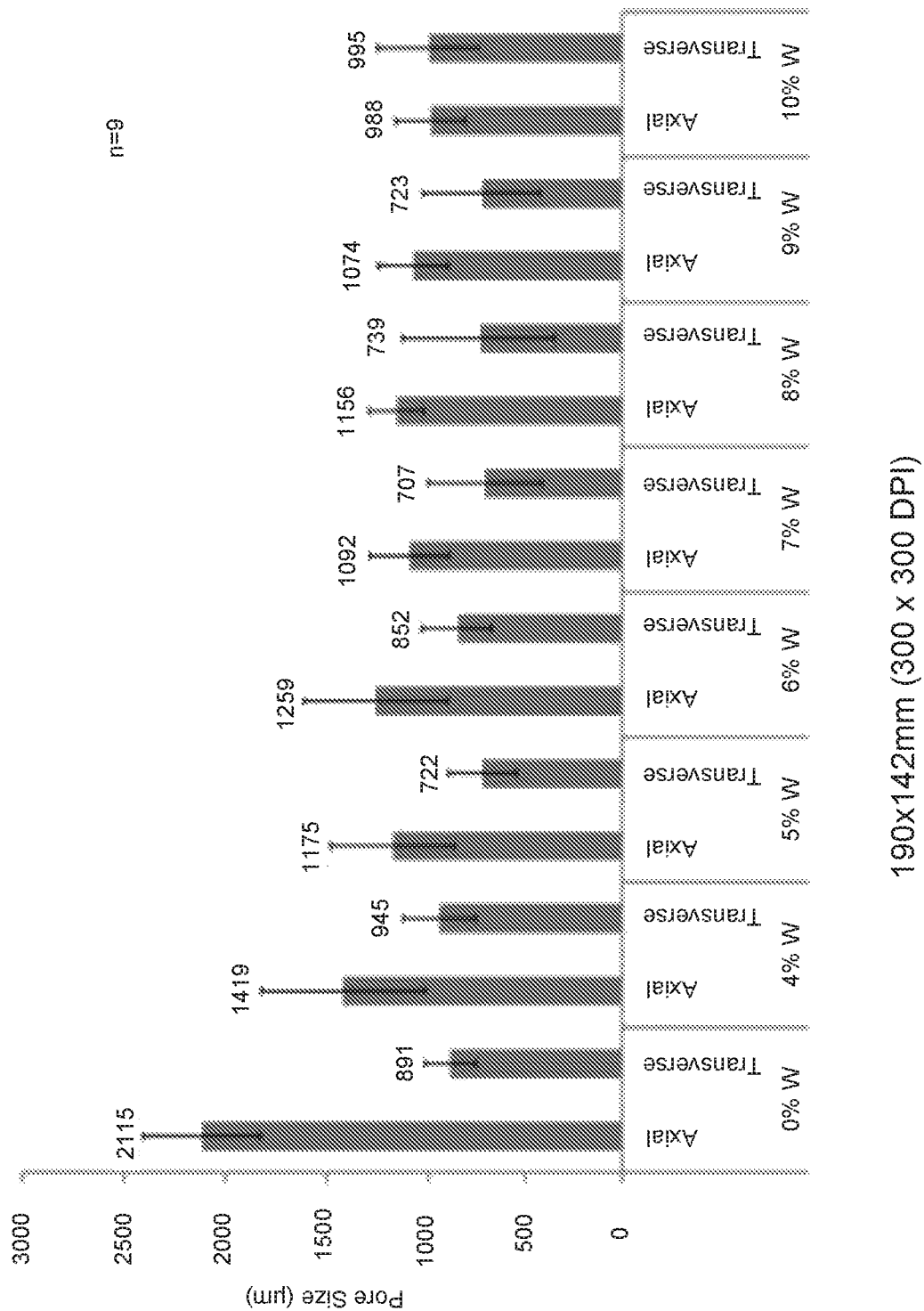
FIG. 4 includes a chart addressing pore sizes in the axial and transverse direction of SMP foams with increasing W content.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photomicrograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical contact.

Applicant determined X-ray visualization of SMP foams is a challenge because the polyurethane SMP material has a density similar to soft tissue and cannot be observed during x-ray fluoroscopy. Therefore delivery of the foam to the aneurysm in a safe and reliable manner is a significant challenge, as guidance by x-ray contrast cannot be used.

However, embodiments introduce radio-opacity to foams using tungsten nanoparticles, which can be incorporated into the polymer using, for example, physical mixing. An embodiment increases filler loading of SMP foams with nanoparticles, allowing for improved particle dispersion resulting in visualization of smaller geometry materials for neurovascular devices that require radio-opacity through soft and hard tissue.

In one aspect, an embodiment features a composition including a shape memory material. Embodiments may include one or more of the following features. The shape memory material includes a polymer. The composition is non-resorbable in a body. The composition may include a therapeutic agent. The composition includes a radiopaque material.

In an embodiment of the invention, very small tungsten (W) nanoparticles (40-60 nm) are incorporated into the compositions to allow the foams to become visible under x-ray. Foams are made with increasing amounts of tungsten that range from 4% to 11% by volume. With increasing concentration of W, there was increased radio-opacity and stiffness. This increased stiffness resulted in improved mechanical properties of the foam.

An embodiment of the invention is directed to a composition featuring a SMP containing a filler. The polymer may be a material that is selected from the group consisting of polyurethane, polynorbomene, polymethylmethacrylate, poly(vinyl chloride), polyethylene, polyisoprene, styrene-butadiene copolymer, a rubber, a polyurea, polyamide, or polysiloxane. In certain embodiments, the polymer comprises at least one isocyanate composition and at least one hydroxyl composition. The isocyanate composition is 1,6-hexamethylene diisocyante (HDI), (2,2,4 and 2,4,4) trimethyl-1,6-hexamethylene diisocyante (TMHDI), methylene diphenyl diisocyanate (MDI), toluene diisocyanate (TDI), or isophorone diisocyanate (IPDI), and the hydroxyl composition is N,N,N',N'-Tetrakis(2-hydroxypropyl) ethylenediamine (HPED) or triethanolamine (TEA).

In certain embodiments, the concentration of filler varies from 0% to 20% by volume of the shape memory polymer. In certain embodiments, the filler is tungsten, tungsten carbide, tungsten oxide, tantalum, gold, palladium, platinum, barium sulfate, zirconium, aluminum oxide, or other high z number nanoparticles (20-10000 nm). In other embodiments, the filler consists of silicate nanoparticles (20-10000 nm). Typically, the filler is radiopaque.

The shape memory foam composition is non-bioabsorbable in a body. In certain embodiments, the composition comprises a therapeutic agent.

Embodiments of the invention are directed to methods of manufacturing a radiopaque shape memory foam composition, the method comprising the steps of: synthesizing an isocyanate premix; curing the isocyanate premix; synthesizing a hydroxyl premix; mixing nanoparticles of a radiopaque material with the cured isocyanate premix one or more surfactants; cooling the nanoparticle/isocyanate mixture to room temperature; adding the hydroxyl premix to the cooled nanoparticle/isocyanate; adding a blowing agent to the nanoparticle/isocyanate/hydroxyl mixture and preparing a homogenous composition; and heating the homogenous composition under vacuum conditions. Typically, the homogenous composition is heated at 90° C., for 10 minutes at a vacuum of −10 cm Hg.

In an embodiment the isocyanate premix comprises a racemic mixture of (2,2,4 and 2,4,4) trimethyl-1,6-hexamethylene diisocyante (TMHDI) and hydroxyl groups containing triethanolamine (TEA) and N,N,N',N'-Tetrakis(2-hydroxypropyl) ethylenediamine (HPED) and the hydroxyl premix comprises hydroxyl groups containing TEA and HPED and catalysts, such as BL-22 and T-131. The radiopaque materials are selected from the group consisting of tungsten, tungsten carbide, tungsten oxide, tantalum, gold, palladium, platinum, barium sulfate, zirconium, aluminum oxide, or other high z number nanoparticles. In certain embodiments, the blowing agent is HFC-245fa,1,1,1,3,3-pentafluoropropane.

For materials to be visualized via x-ray imaging techniques, such as fluoroscopy, they must be able to stop more x-rays than the surrounding environment. For visualization, materials must be of different densities in order to see a difference between them. For example, a medical device must be denser than the surrounding tissues, in order to be seen using x-ray based technology. If the device is visible while in the body, it is said that the device is radiopaque.

Low density SMP foams in small volumes are not inherently dense enough to have the ability to block more x-rays than soft tissues. As such, prior to adding small metallic particles they do not possess radio-opacity. This serves as a challenge for the use of these foams in implantation by less invasive techniques, such as placement by catheter, or endovascular placement, of a device to treat diseases of the vasculature.

In an effort to induce radio-opacity, embodiments of the invention incorporate very small W nanoparticles (40-60 nm) to allow for the foams to become visible under x-ray. Foams were made with increasing amounts of W that ranged from 4% to 11% by volume. The resulting radio-opaque foam formulations were characterized to determine their physical and mechanical properties. These characterizations included porosity, cell uniformity, glass transition temperature ($T_1$) tensile properties, volume recovery and expansion, and actuation time. Fluoroscopy images of the crimped foam were obtained for qualitative determination of radio-opacity. Additionally, quantitative X-ray density of each composition was measured and compared to a traditional aneurysm treatment device, a platinum coil, or Guglielmi Detachable Coil (GDC), as a control. With increasing concentration of W, there was increased radio-opacity and stiffness. This increased stiffness resulted in improved mechanical properties of the foam.

These radiopaque foams of the claimed invention can be used for a variety of vascular devices, such as a foam aneurysm-filling device. By varying the concentration of W, it is possible to adjust the radio-opacity of the foam for its application. For example, foam used for filling a cerebral aneurysm will contain more tungsten nanoparticles in order to be visible through the skull compared to a foam of similar dimensions that will be imaged only through soft tissue.

Furthermore, in addition to increasing the radio-opacity, filler incorporation serves to mechanically strengthen the material and increase the overall toughness of the composite.

In certain embodiments, the radio-opaque foam of the invention can be used in a foam over coil cerebral aneurysm device. In this embodiment, the device is inserted into the aneurysm space through a catheter and the foam is passively actuated to occlude the aneurysm space. Nickel-titanium wires can be threaded through pre-cut foam cylinders which are then crimped around the wire to a small diameter which would be able to pass through a catheter. The device does not require any additional radio-opaque markers or contrast agents during delivery because the W-doped crimped foam provides sufficient visibility under x-ray.

In another embodiment, the radiopaque SMP foam is used as a treatment for abdominal aortic aneurysms. Specific foam geometries are cut out of the bulk foam block and crimped to a small diameter in order to fit through the catheter.

Embodiments of radio-opaque SMP foams improve applications for aneurysm devices and may be used in drug delivery devices and implants. The use of contrast injections for aneurysm occlusion devices may be eliminated, or significantly reduced. W-doped SMP foams have an increased toughness compared to their non-opaque counterparts which allows for SMP foam use for applications with some weight bearing and mechanical loading, such as orthopedic applications.

Previously synthesized radio-opaque SMP foams used tungsten micro particles (<1 micron) with up to 4% by volume loading. These foams have a different chemical composition compared to the W nanoparticle doped foams, which results in improved mechanical properties.

Additionally, W microparticles can only be loaded into the foam up to 4% by volume before they disrupt the foaming process and result in the development of geode-style foams (i.e., foam having a massive pore with an exterior skin), which are hollow and have non-homogenous pores. In other words, microparticles are so big that beyond 4% by volume they fail to adequately disperse. Instead, they aggregate with one another and disrupt foaming (e.g., disrupt formation of the struts of the cells). The disruption is so severe the structural integrity of the foam is compromised and the foam collapses or has too little stiffness to perform any meaningful support to other structures (e.g., tissues). However, W nanoparticles provide better loading and dispersion than the microparticles, which allows concentrations up to 11% W by volume to be attained while still maintaining a uniform foam morphology. This, in turn, improves the radio-opacity of the foams compared to the microparticle loaded SMP foams. For example, due to their dispersion and size, W nanoparticles actually form within the struts of the cells, and may even aggregate within the pores located within the individual struts. However, the aggregation is tolerable and still results in smooth struts that have structural integrity (e.g., FIG. 5b). In other words, the struts do not bellow or otherwise project around the nanoparticles. In such a case, one may not see a difference in the outer profile of a strut portion having no nanoparticle and another strut portion (of that same strut) that indeed does have a nanoparticle (or an aggregation of nanoparticles).

In certain embodiments of the invention, foam containing 7% W or higher v/v are sufficiently visible through dense structures within the body, such as the skull in dimensions viable as a neuroendovascular treatment device. Subsequent testing of these materials using mechanical and thermal characterization has shown that the glass transition temperature (Tg) increases proportional to tungsten loading. This suggests that the foams are becoming stiffer and tougher from the addition of the radiopaque nanoparticles, resulting in a composite material.

In an embodiment of the invention, SMP foam synthesis occurs using the following steps:
1. An isocyante (NCO) premix is synthesized with a racemic mixture of (2,2,4 and 2,4,4) trimethyl-1,6-hexamethylene diisocyante (TMHDI) and 35% hydroxyl groups containing triethanolamine (TEA) and N,N,N',N'-Tetrakis(2-hydroxypropyl) ethylenediamine (HPED). This mixture is cured for 2 days before further use;
2. A hydroxyl (OH) premix is synthesized with 65% hydroxyl groups containing TEA and HPED along with DI water and catalysts, such as BL-22 and T-131;
3. Tungsten nanoparticles are weighed out in the foam container and the appropriate amount of NCO premix is added, along with surfactants such as, but not limited to, DC 198 and DC 5943. These components are mixed into a homogenous solution and allowed to cool to room temperature;
4. The OH premix is added to the foam container and mixed again, followed by the addition of a blowing agent, such as Enovate, after which further mixing is needed until a homogenous mixture is achieved;
5. The final mixture is poured into a larger foaming container and placed in the oven at 90° C., for 10 minutes while gradually pulling vacuum down to −10 cm Hg.

Other embodiments may change the order. For example, W may be added to the OH premix, all of which is then combined with the NCO premix followed by step (5) above.

Working Examples

N,N,N',N'-Tetrakis(2-hydroxypropyl)ethylenediamine (HPED, 99%; Sigma-Aldrich Inc.), triethanolamine (TEA, 98%; Sigma-Aldrich Inc.), trimethyl-1,6-hexamethylene diisocyanate, 2,2,4- and 2,4,4-mixture (TMHDI, TCI America Inc.), DC 198 (Air Products and Chemicals, Inc.), DC 5943 (Air Products and Chemicals, Inc.), T-131 (Air Products and Chemicals, Inc.), BL-22 (Air Products and Chemicals, Inc.), Enovate 245fa Blowing Agent (Honeywell International, Inc.) and deionized (DI) water (>17 MΩ cm purity; Millipore water purifier system; Millipore Inc.) were used as received. Tungsten nanoparticles (W, 99.95%, 40-60 nm (US Research Nanomaterials Inc.) were dried for 12 hours, under vacuum, prior to foam synthesis.

SMP foam synthesis was conducted using the protocol described by Hasan et al. W nanoparticles (40-60 nm) were dispersed in the isocyanate (NCO) pre-polymer, prior to foam blowing, at 4% to 11% by volume. TMDHI comprised the NCO pre-polymer along with 35% of alcohols (HPED and TEA). Molar equivalent of hydroxyl (OH) pre-polymer was added to the mixture including catalysts, surfactants, and Enovate. The foam was cured at 90° C. under vacuum at −10 mmHg for 10 minutes. The SMP foam was allowed to cool to room temperature before further characterization. FIG. 1 shows the weight percent of each component used in foam blowing. Three foam batches were synthesized and characterized for duplicity.

Density and Porosity

Density measurements were conducted on foam blocks acquired from the top, middle, and bottom section of the foam. Mass of the foam block was recorded and length, width, and height values were measured three times using a digital caliper. Porosity was calculated using Equation 1.

$$\text{Porosity (\%)} = \left(\frac{\rho_{neat} - \rho_{foam}}{\rho_{neat}}\right) * 100 \qquad \text{(Eq. 1)}$$

Scanning Electron Microscopy (SEM) and Pore Sizes

Cell structure was determined by cutting thin slices of the bulk foam in the axial and transverse direction. The samples were mounted onto a stage and sputter coated for 60 seconds at 20 mA with gold using Cressington Sputter Coater (Ted Pella, Inc., Redding, Calif.). The samples were then imaged using Joel NeoScope JCM-5000 Scanning Electron Microscope (Nikon Instruments, Inc., Melville, N.Y.) at 10-13× magnification under high vacuum and 5-10 kV current. Pore sizes (FIG. 4) were calculated by measuring the cell diameter, using Image J software (NIH, Bethesda, Md.), in the axial and transverse direction for each SEM image.

Transmission Electron Microscopy (TEM)

A small piece (2 mm×4 mm) of the sample was cut and embedded in the flat mold with Polybed 812 (Polysciences, Inc., Warrington, Pa.) and polymerized at 60° C., overnight. The sample resin block was sectioned at room temperature, using Leica UC6 microtome (Leica Microsystems, Wetzlar, Germany) and DiATOME diamond knives (DiATOME, Hatfield, Pa.). Ultra-thin sections (70 nm) were examined by JEOL 1200EX II electron microscopy (Jeol, Peabody, Mass.).

X-Ray Imaging

An opacity frame was developed by mounting filler-loaded foam samples onto a clear polycarbonate sheet. 2 mm foam cylinders were threaded over an 89 μm diameter nickel-titanium (Nitinol) wire (NDC, Fremont, Calif.). A Guglielmi Detachable Coil (GDC) used as the control for this experiment because it is a platinum coil which is considered a standard for aneurysm treatment. The opacity frame was placed under a porcine head and imaged using a Philips Allura Xper FD 20 C-arm System at 63 kV and 382 mA through soft and hard tissue. Images of the opacity frame were collected under porcine jaw and neck for evaluating foam visibility at multiple sites compared to the control.

X-Ray Density (X.D.)

X-ray images of the opacity frame were acquired on a Bruker In-Vivo Xtreme multimodal preclinical imaging system (Bruker BioSpin Corp., Billerica, Mass.) outfitted with a 4 MP back-thinned, back-illuminated 4MP CCD detector. X-rays were collected with an exposure time of 1.0 s, where the f-stop=1.40, FOV=153.0 mm, vertical and horizontal resolution=377 ppi and X-ray energy=45 KVP. Images were edited using Bruker molecular imaging software.

The background was subtracted using an illumination correction reference. To quantify the x-ray density for each sample, a length of 0.50 cm was selected along each sample in the X-ray image as the region of interest. Greater than 70 pixels of X-ray density (X.D.) were taken within the region of interest for each foam utilizing Bruker Molecular Imaging Software. From these measurements, a mean and standard deviation of the X.D. was calculated.

Differential Scanning Calorimetry (DSC)

The glass transition temperature (Tg) of the foams (n=5) was determined under dry and wet conditions. For dry Tg, foam samples (3-8 mg) were used which were stored in a dry container with desiccant, prior to analysis. A Q-200 DSC (TA Instruments, Inc., New Castle, Del.) was used to attain the thermogram for our foams. The first cycle consisted of decreasing the temperature to −40° C. at 10° C.·min-1 and holding it isothermal for 2 minutes. The temperature was then increased to 120° C. at 10° C.·min-1 and held isothermal for 2 minutes. In the second cycle, the temperature was reduced to −40° C. at 10° C.·min-1, held isothermal for 2 minutes, and raised to 120° C. at 10° C.·min-1. Tg was recorded from the second cycle based on the inflection point of the thermal transition curve using TA instruments software. The aluminum tin was not vented during this step. For wet Tg, foam samples (3-8 mg) were submerged in RO water at 50° C. for 5 minutes to allow full plasticization. After the samples were removed from water, they were pressed dry with Kim Wipes (Kimberly-Clark Professionals, Roswell, Ga.), weighed, and placed in an aluminum pan sealed with an aluminum lid that was vented. Q-200 DSC was used to cool the samples to −40° C., hold them isothermal for 2 minutes, and heat them to 80° C. at 10° C.·min-1. TA instruments software was used to generate the thermogram and acquire the Tg, after water plasticization, using the average inflection point of the thermal transition.

Tensile Testing

Uniaxial tensile loading tests were carried out using an Insight 30 Material Tester (MTS Systems Corporation, Eden Prairie, Minn.) at a constant strain rate of 5 mm/min at room temperature. 10 foam samples with (L=25 mm, W=15 mm, H=3 mm) were cut from the bulk material. Wood tabs were secured on each end of the foam, using epoxy, to prevent sample deformation in the grips during testing. Tensile strength (kPa), Young's modulus (kPa), toughness (J·m-3) and strain at break (%) were determined per sample using the stress-strain curve.

Actuation Studies

Cylindrical foam samples (n=3) with a diameter of 2 mm and a height of 1 cm were cut. A 203.20 μm diameter nickel-titanium (Nitinol) wire (NDC, Fremont, Calif.) was inserted through the center of the sample along its length to serve as a stabilizer. The foam samples were radially compressed to their smallest possible diameter using ST 150-42 stent crimper (Machine Solutions, Flagstaff, Ariz.) by heating the material to 100° C., holding it isothermal for 15 minutes, and programming the foams to the crimped morphology. Initial foam diameter was measured and recorded for each sample using Image J software (NIH, Bethesda, Md.). The foams were placed in a water bath at 37° C. and images were taken at 30 seconds, 1 minute and every minute thereafter till 15 minutes, followed by one image every 5 minutes thereafter till 30 minutes.

Foam diameter was measured, at each time point, using Image J software. The foams were then placed in a 70° C. RO water bath, removed after 20 minutes, and allowed to cool to room temperature. The final diameter of the samples was measured and recorded using Image J software. Percent volume recovery was calculated using Equation 2 and volume expansion was calculated using Equation 3.

$$\text{\% Volume Recovery} = \left(\frac{\text{Recovered diameter}}{\text{Original diameter}}\right)^2 * 100 \qquad \text{(Eq. 2)}$$

$$\text{Volume Expansion} = \left(\frac{\text{Recovered diameter}}{\text{Compressed diameter}}\right)^2 \qquad \text{(Eq. 3)}$$

Results

Density and Porosity

Foam density increased markedly, from 0.013 to 0.060 g·cm-3, with greater W incorporation due to the added mass within the foam struts per block, Table 2. All compositions, however, maintained low densities, indicative of the foams retaining high surface area to volume ratios. Neat polymer density also increased with W addition (FIG. 2), from 1.0 to 3.0 g·cm-3, indicating the material become heavier with filler content without variation from foaming agents. Porosity calculations (FIG. 2) showed high porosity (>98%) for all compositions with low standard deviation, indicating cell uniformity throughout the bulk foam. These results confirm the development of lightweight foams with high surface area suitable for embolic occlusion devices.

Scanning Electron Microscopy (SEM) and Pore Sizes

Figure 5A:
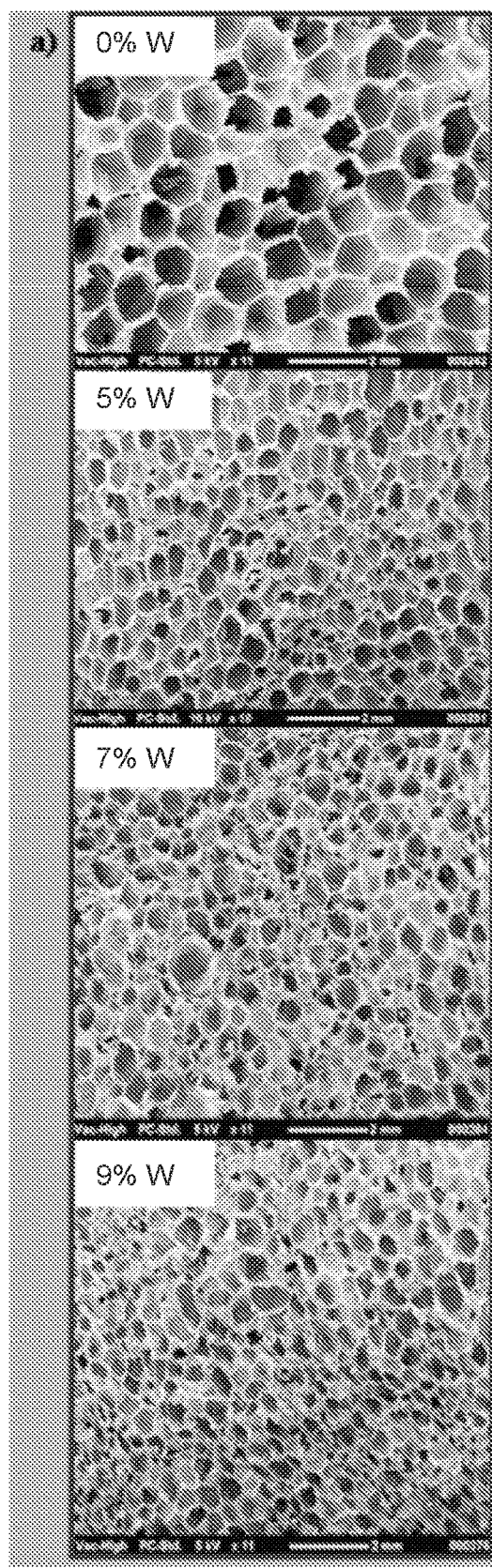
FIG. 5a includes SEM images of SMP nanocomposites at 10-11× magnification.

SEM images of the foams, FIG. 5a, indicate smaller pore sizes with greater tungsten incorporation. Nanoparticles serve as nucleating sites during the gas blowing foaming process, which increases the number of bubbles generated in the polymer matrix. This, in turn, causes smaller bubble generation and ultimately smaller pore sizes throughout the bulk foam. Note that, while pore density and volume change with loading, overall porosity remains relatively constant. Additionally, pore diameter measurements show the pores are becoming more isotropic compared to the control foam where the pores are larger in the axial foaming direction than the transverse direction. Axial lengthening is not shown in FIG. 5a (a transverse cross section), however this does occur. Nanofiller addition increased the polymer viscosity prior to foam blowing which translates to smaller pore sizes of the bulk foam due to slower gas release within the increasingly viscous polymer solution. Tungsten nanoparticles can therefore be used to control foam morphology and serve as a tool to regulate pore sizes (FIG. 4).

Transmission Electron Microscopy (TEM)

Figure 5B:
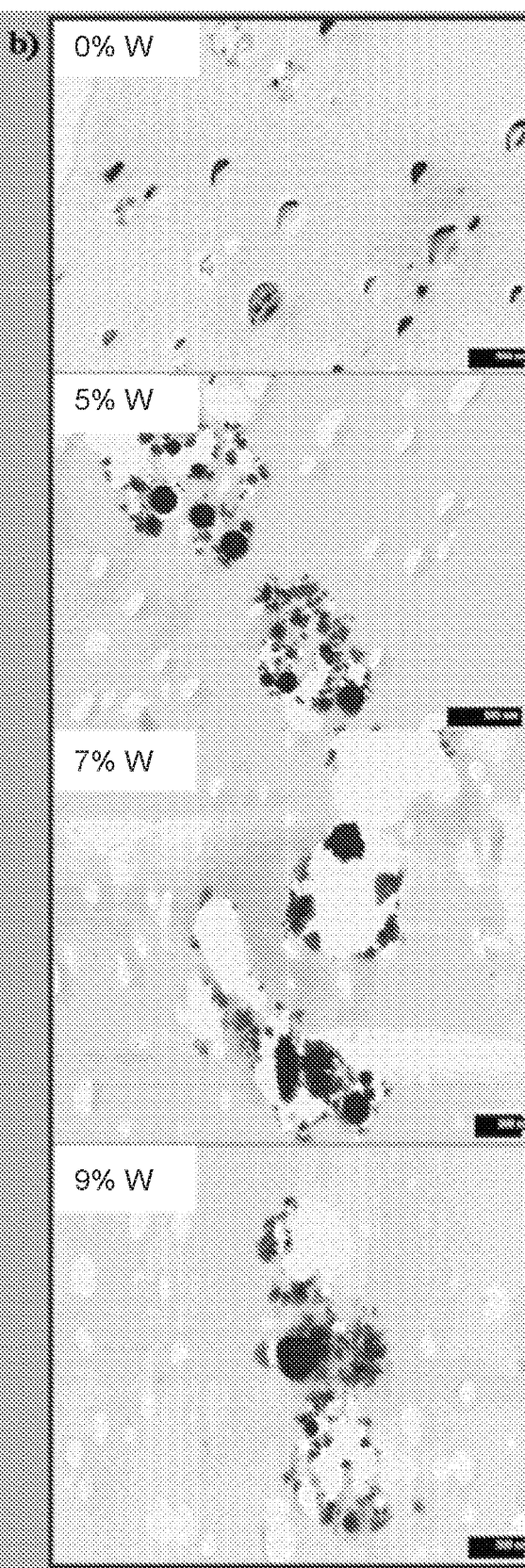
FIG. 5b includes TEM images of the SMP nanocomposites showing filler aggregates.

Incorporation of W nanoparticles into the SMP system resulted in aggregate formation at the nanoscale even at low concentrations, FIG. 5b. TEM image of the control (0% W) foam shows nanopores within the polymer struts which indicate the occurrence of these defects as a part of the foaming process rather than as a result of filler incorporation. However, 5% W, 7% W, and 9% W composites have filler aggregates in the polymer struts that imply less than complete dispersion of the nanoparticles with physical mixing.

X-Ray Imaging

Figure 6:
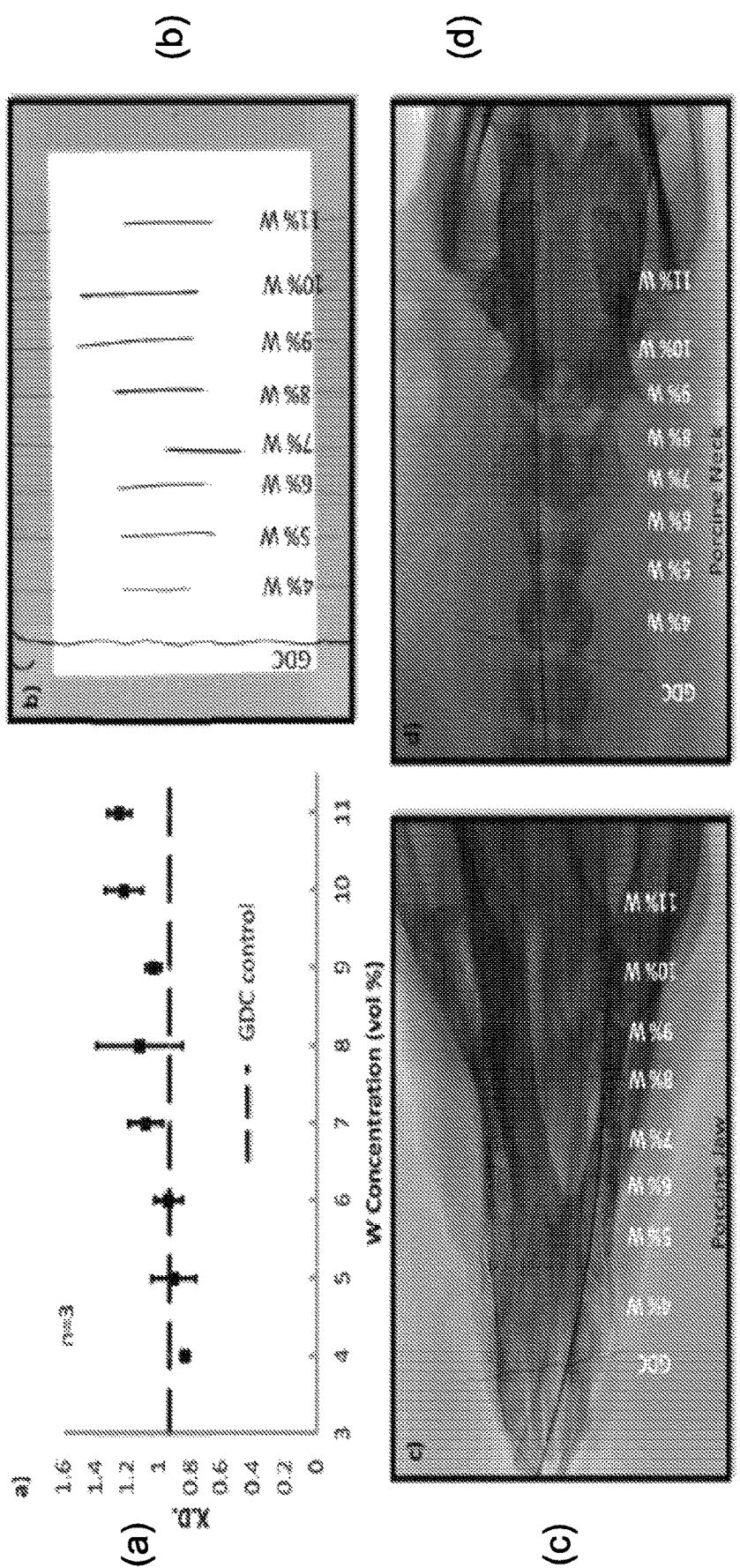
FIG. 6a depicts X-ray density of the SMP foams with increasing W content.
FIG. 6b depicts design of the frame mounted with crimped SMP foam over nitinol wire.
FIG. 6c depicts X-ray image of the SMP foams through porcine jaw.
FIG. 6d depicts X-ray image of the SMP foams through porcine neck.

Sufficient x-ray visibility was achieved for SMP nanocomposites with W loading greater than 6%, FIG. 6a. Crimped foams attenuated x-rays through soft and hard tissue of the porcine head at various locations, suggesting acceptable visibility through qualitative analysis.

X-Ray Density (X.D.)

Quantitative evaluation of foam visibility was conducted via X.D. analysis (FIGS. 6a, 6b, 6c, 6d). With increasing W loading, the crimped SMP attenuates x-ray more effectively, increasing from 0.8 to 1.2 at 45 KV. For SMP foams with greater than 6% W, average X.D. was larger than the GDC control (0.9). Filler addition successfully imparted radio-opacity to the polymer system such that it will allow for use of smaller foam diameters without compromising x-ray visibility.

Differential Scanning Calorimetry (DSC)

Thermal characterization of the foams revealed increasing transition temperatures with greater W loading (FIG. 2). Dry Tg of the SMP foams increased by 10° C. while wet Tg increased by 7° C. with higher filler content. Nanoparticle incorporation restricted polymer mobility at the molecular level and increased the number of physical crosslinks within the SMP network, therefore requiring greater heat input for the polymer to transition from the glassy to the rubbery state. This finding serves as a method for tuning thermal properties of the system for other applications that require a specific actuation temperature.

Tensile Testing

Figure 7A:
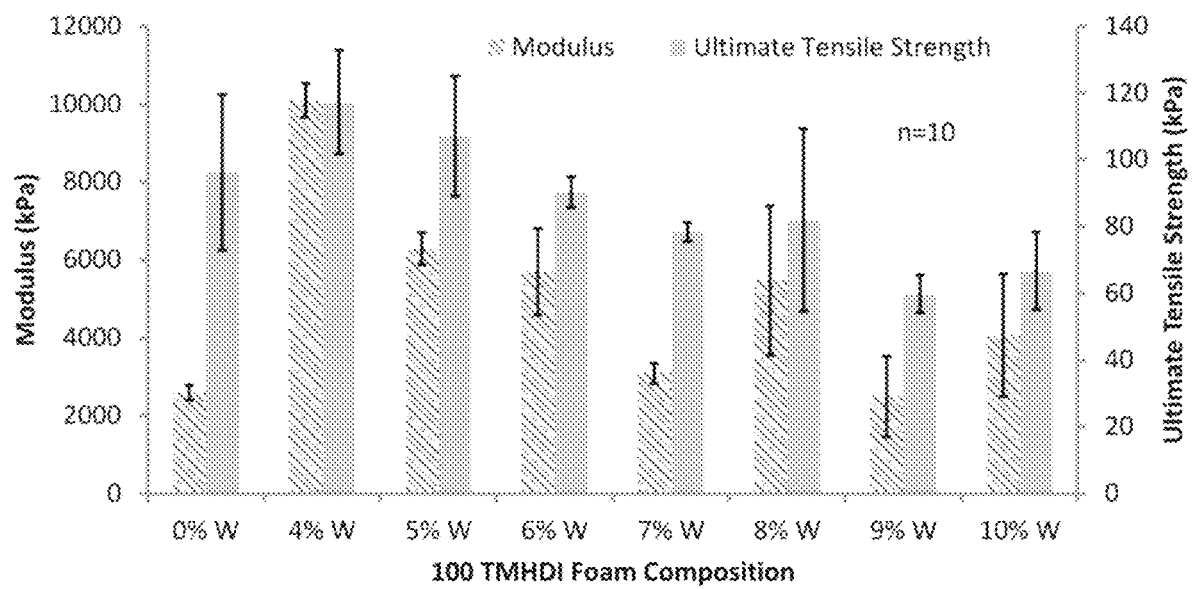
FIG. 7a depicts mechanical properties (modulus) of the SMP foams with increasing W content.
Figure 7B:
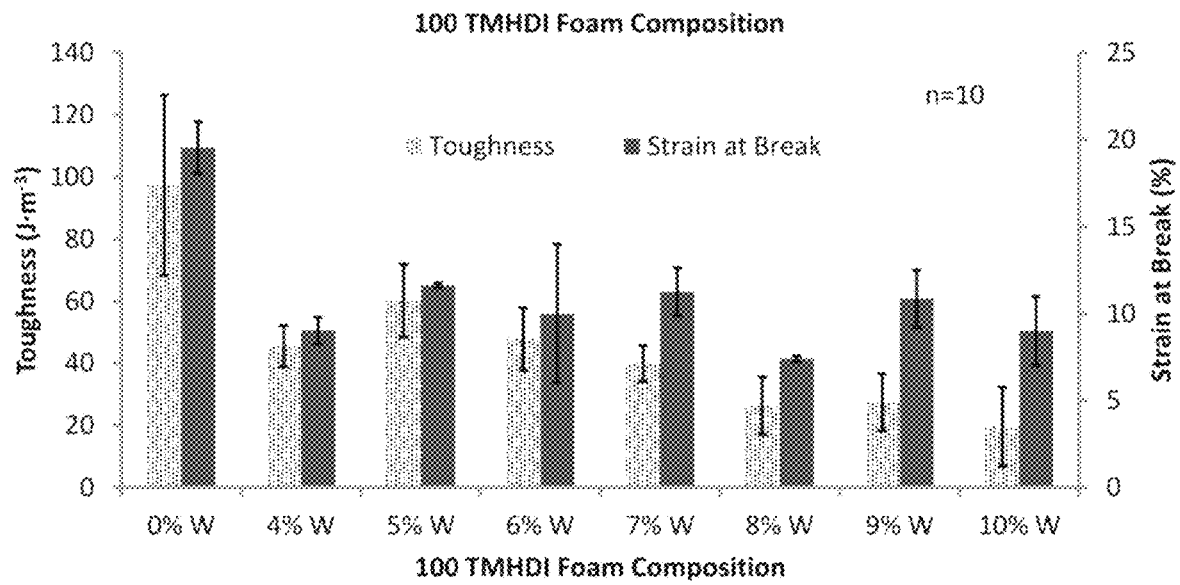
FIG. 7b depicts mechanical properties (toughness) of the SMP foams with increasing W content.

Increasing W concentration in SMP foams changed mechanical properties compared to the control (FIGS. 3, 7a, and 7b). An increase in Young's modulus can be observed, from 2600±200 kPa to 10100±400 kPa, for 4% W foams, indicating greater material stiffness. However, higher filler content resulted in decreasing stiffness due to disruption of the polymer matrix. Similarly, the tensile strength of the foams increased at 4% W, from 96±2 kPa to 120±20 kPa, however beyond this concentration the mechanical properties decrease as a result filler agglomerates replacing the polymer within the foam struts. Filler agglomerates within the foam struts resulted from poor dispersion due to relatively agglomerated starting materials, e.g. tungsten nanopowder. Toughness and strain at break of the SMP material also decreased compared to the control foam because of increased stiffness and aggregate formation due to high filler loading (FIG. 7b). Overall, with higher W nanoparticle loading the foams became harder due to increased stiffness and decreasing polymer content within the struts. Additionally, variation in tensile strength and Young's modulus of the higher loaded foams occurred due to changes in foam morphology as a result of heterogeneous pore sizes.

Actuation Studies

Figure 8:
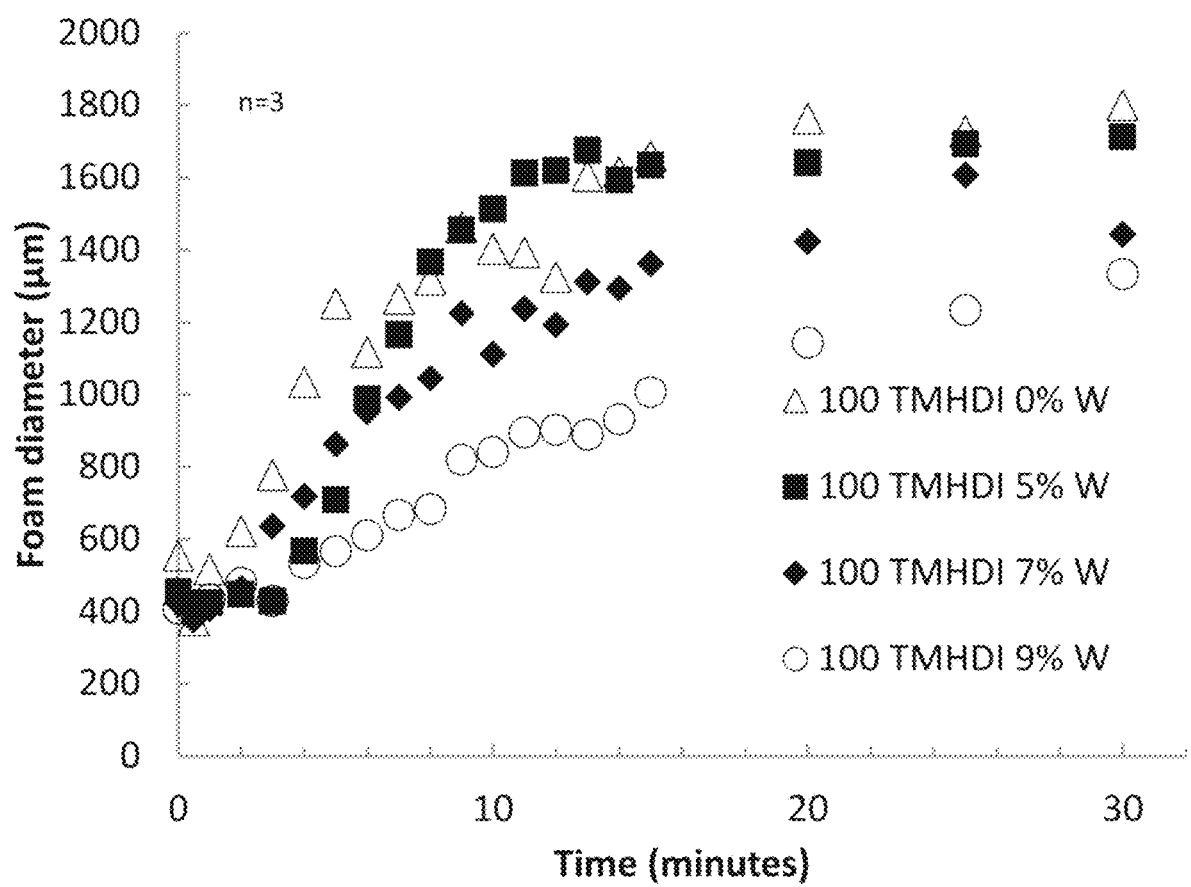
FIG. 8 depicts actuation kinetics of SMP foams at physiological temperature

Nanoparticle addition altered passive actuation kinetics of SMP foams at physiological temperature (FIG. 8). The control foam actuated within 4 minutes, as indicated by the inflection point of the plot. However, with increasing W loading the SMP experienced longer actuation times of 6, 8, and 10 minutes for 5% W, 7% W, and 9% W foams, respectively, which is reasonable given their increasing thermal transitions. Volume recovery (FIG. 2) of the foams remained greater than 80% for all foams, however, considerably less than the control foam due to increased molecular restrictions on the network mobility. Similarly, volume expansion of the foams decreased with W addition, from 63x±14 to 21x±4, for the control foams and 4% W loaded foams, respectively.

Discussion

SMP foam nanocomposites were synthesized with inherent radio-opacity by incorporating W nanoparticles within the polymer matrix during OH premix synthesis. W is a high Z number element which allowed it to effectively attenuate x-rays and impart visibility to SMP foams through soft and hard tissue. A smaller foam geometry was used for neurovascular applications, therefore higher filler loading was required to make the foams radiopaque. W concentrations greater than 6% resulted in sufficient foam visibility, when crimped, and had greater X.D. compared to the GDC control. Additionally, the SMP foams maintained their low density and high porosity, making them desirable for aneurysm occlusion devices due to their large volume expansion and high surface area. W nanoparticles served as a tool for controlling viscosity of the foam mixture and provided nucleation sites, which resulted in smaller and more isotropic pores with greater filler loading. This finding is critical for controlling the overall foam morphology and serves as a platform for material development for new medical applications that require specific pore sizes in polyurethane scaffolds. This is critical because foam morphology is largely dependent on the viscosity of the premix (pore size), mold geometry (pore shape), and bubble nucleation (# of pores/fine pores). These nanofillers can be used to alter all of these properties.

Filler dispersion improved significantly with nanoparticle content compared to the microcomposites developed by Rodriguez et al. W nanoparticles dispersion within the foam matrix was more homogeneous, compared to W microparticles, as seen by the lack of filler agglomerates within the struts and the foam membranes in the SEM images (FIG. 5a). However, filler aggregation still occurred on the nanoscale (FIG. 5b), indicating incomplete nanoparticle mixing into the foam matrix.

Thermal characterization of the foams showed increasing transition temperature, under dry and wet conditions, for foams with W loading greater than 5%. The nanoparticles restricted network mobility, thereby increasing polymer stiffness, and required higher temperature for the polymer to transition from the glassy to rubbery state. W addition provided greater control over the thermal properties of the SMP system. This functions as a tool for tuning of the foams and prevention of premature water plasticization of foams in the catheter during device delivery. Similarly, passive actuation time of the foams increased with filler addition due to slower foam plasticization by water. Thus, W nanoparticles have use providing greater control over the actuation kinetics of SMP foams to achieve longer working times for clinical applications.

Volume recovery and expansion of the SMP foams decrease with greater W loading. However, the foams recover to 80% of their original diameter and expand up to 40× their crimped diameter, maintaining their efficacy for aneurysm occlusion. Lastly, mechanical properties of the SMP nanocomposites diminished with filler addition due to a large percentage of the polymer strut being replaced by W. While nanoparticles increased material stiffness and strength up to 4% W loading, an opposite effect was observed on toughness and strain-to-failure at all concentrations. Notably the foams were tested below Tg. This could have a negative effect on mechanical properties as, above Tg, the rubbery polymer would align around the filler particles and provide higher toughness and strain-to-failure response.

In conclusion, radiopaque SMP foam nanocomposites were developed with high W loading, up to 10% by volume, and high porosity for aneurysm occlusion applications. W nanoparticles successfully introduced radio-opacity of the foams, using x-ray fluoroscopy, and made the device visible during transcatheter delivery and deployment within the aneurysm. SMP foam nanocomposites also exhibited tunable thermal and mechanical properties along with delayed actuation, providing greater control over the actuation kinetics of the system.

An embodiment includes a kit with foams having differing W filler content percentages. A kit may include a doped foam within a sheath and coupled to a pusher wire. Kits may be differentiated by application such that, for example, one kit for neurovascular applications has a foam doped with W at 6%, 7%, 8%, 9%, or 10% by volume or more, whereas a kit for peripheral vascular applications has a foam doped with 3%, 4%, or 5% by volume.

Example 1 includes a composition featuring a shape memory polymer containing a filler.

Example 2 includes the composition of example 1, wherein the polymer is a solid polymer or a foam.

Example 3 includes the composition of example 1, wherein the polymer is a material selected from the group consisting of polyurethane, polynorbornene, polymethylmethacrylate, poly(vinyl chloride), polyethylene, polyisoprene, styrene-butadiene copolymer, and a rubber.

Example 4 includes the composition of example 1, comprising at least one isocyanate composition and at least one hydroxyl composition.

Example 5 includes the composition of example 4, wherein the isocyanate composition is 1,6-hexamethylene diisocyante (HDI), (2,2,4 and 2,4,4) trimethyl-1,6-hexamethylene diisocyante (TMHDI), methylene diphenyl diisocyanate (MDI), toluene diisocyanate (TDI), or isophorone diisocyanate (IPDI).

Example 6 includes the composition of example 5, wherein the composition comprises a mixture of one or more isocyanates in any ratio and combination.

Example 7 includes the composition of example 4, wherein the hydroxyl composition is N,N,N',N'-Tetrakis(2-hydroxypropyl) ethylenediamine (HPED) or triethanolamine (TEA).

Example 8 includes the composition of example 7, wherein the composition comprises a mixture of one or more polyols in any ratio and combination.

Example 9 includes the composition of example 1, wherein the polymer is a polyurea, polyamide, or polysiloxane.

Example 10 includes the composition of example 1, wherein the concentration of filler varies from 0.5% to 20% by volume of the shape memory polymer.

Example 11 includes the composition of example 1, wherein the filler is tungsten, tungsten carbide, tungsten oxide, tantalum, gold, palladium, platinum, barium sulfate, zirconium, aluminum oxide, or other high z number nanoparticles (20-10000 nm).

Example 12 includes the composition of example 10, wherein the composition comprises a mixture of one or more fillers in any ratio and combination.

Example 13 includes the composition of example 1, wherein the filler consists of silicate nanoparticles (20-10000 nm).

Example 14 includes the composition of example 1, wherein the filler is radiopaque.

Example 15 includes the composition of example 1, wherein the composition is non-bioabsorbable in a body.

Example 16 includes the composition of example 1, wherein the composition comprises a therapeutic agent.

Example 17 includes the composition of example 1, wherein the filler increases the toughness of the polymer.

Example 18: The composition of example 1, wherein the filler increases the density of the polymer.

Example 19 includes the composition of example 1, wherein the filler decreases the pore size of the polymer foam.

Example 20 includes the composition of example 1, wherein the filler increases the wet and dry glass transition temperature of the polymer.

Example 21 includes the composition of example 1, wherein the filler increases the time required to actuate the polymer and decreases the volume recovery of the polymer.

Example 22 includes a method of manufacturing a radiopaque shape memory foam composition, the method comprising the steps of: synthesizing an isocyanate premix; curing the isocyanate premix; synthesizing a hydroxyl premix; mixing nanoparticles of a radiopaque materials with the cured isocyanate premix one or more surfactants; cooling the nanoparticle/isocyanate mixture to room temperature; adding the hydroxyl premix to the cooled nanoparticle/isocyanate; adding a blowing agent to the nanoparticle/isocyanate/hydroxyl mixture and preparing a homogenous composition; and heating the homogenous composition under vacuum conditions.

Example 23 includes the method of example 22, wherein the isocyanate premix comprises a racemic mixture of (2,2,4 and 2,4,4) trimethyl-1,6-hexamethylene diisocyante (TMHDI) and hydroxyl groups containing triethanolamine (TEA) and N,N,N',N'-Tetrakis(2-hydroxypropyl) ethylenediamine (HPED).

Example 24 includes the method of example 22, wherein the hydroxyl premix comprises hydroxyl groups containing TEA and HPED and catalysts, such as BL-22 and T-131.

Example 25 includes the method of example 22, wherein the radiopaque materials are selected from the group consisting of tungsten, tungsten carbide, tungsten oxide, tantalum, gold, palladium, platinum, barium sulfate, zirconium, aluminum oxide, or other high z number nanoparticles.

Example 26 includes the method of example 22, wherein the blowing agent is HFC-245fa,1,1,1,3,3-pentafluoropropane.

Example 27 includes the method of example 22, wherein the homogenous composition is heated at 90° C., for 10 minutes at a vacuum of −10 cm Hg.

Example 1a includes a system comprising: a neurovascular implant including a longitudinal axis and a maximum outer diameter, taken orthogonal to the longitudinal axis, which is no greater than 0.035 inches; wherein (a) the implant includes a shape memory polymer foam comprising cells formed by struts, (b) the struts each include tungsten (W) nanoparticles having a maximum diameter that is less than 70 nm; and (d) the foam is crimped around a metal backbone.

For example, the implant may include a sheath portion over the foam and a nitinol metal backbone. The sheath may be less than 0.035 inches in order to navigate the tortuous vasculature of the human head. Also, FIG. 5(b) shows horizontal cross sections of a single strut taken at extremely high magnification. The black portions are W nanoparticles. Please note that the majority of any cross section or any axis extending across any cross section is comprised of non-black polymer. The W nanoparticles take up little of the cross section and therefore do not degrade the structure integrity of the foam by substituting W for polymer. If this were to show microparticles at the same magnification one would see the majority (>50%) of the cross section (or any axis extending across the cross section) occupied by the relatively large microparticle or aggregated microparticles.

Another version of Example 1a includes a system comprising: a neurovascular implant including a longitudinal axis and a maximum outer diameter taken orthogonal to the longitudinal axis; wherein (a) the implant includes a shape memory polymer foam comprising cells formed by struts, (b) the struts each include tungsten (W) nanoparticles having a maximum diameter that is less than 70 nm, (d) the foam is crimped around a backbone, and (e) the maximum outer diameter of the implant, when the foam is crimped, is no greater than 0.035 inches.

Another version of Example 1a includes a system comprising:a vascular implant including a longitudinal axis and a maximum outer diameter, taken orthogonal to the longitudinal axis; wherein (a) the implant includes a shape memory polymer foam comprising cells formed by struts, (b) the struts each include tungsten (W) nanoparticles having a maximum diameter that is less than 70 nm; and (d) the foam is crimped around a backbone.

The backbone may include a metal, polymer, nitinol, and the like. Some embodiments include no backbone.

Example 2a includes the system of example 1a, wherein foam includes at least 6% W nanoparticles by volume and no more than 10% W nanoparticles by volume.

Another version of Example 2A includes the system of example 1a, wherein foam includes at least 4% W nanoparticles by volume and no more than 10% W nanoparticles by volume.

Example 3a includes the system of example 2a, wherein the foam, which is crimped around the backbone, has an X-ray density (X.D.) of at least 1.0 Hounsfield units (HU) when imaged at 45 KV.

Radiodensity (or radiopacity) refers to the relative inability of electromagnetic radiation, particularly X-rays, to pass through a particular material. Though the term radiodensity is more commonly used in the context of qualitative comparison, radiodensity can also be quantified according to the Hounsfield scale, a principle which is central to X-ray computed tomography (CT scan) applications. On the Hounsfield scale, distilled water has a value of 0 Hounsfield units (HU), while air is specified as −1000 HU.

Example 4a includes the system of example 2a, wherein the foam includes a polymer selected from the group consisting of polyurethane, polynorbomene, polymethylmethacrylate, poly(vinyl chloride), polyethylene, polyisoprene, and styrene-butadiene copolymer.

Example 5a includes the system of example 4a, wherein: the struts include a first strut that has a longitudinal axis that generally defines a length of the first strut and a horizontal axis that generally defines a width of the first strut;
the horizontal axis intersects at least one the W nanoparticles and a portion of the polymer; and
the majority of the width of the first strut includes the polymer and not the at least one of the W nanoparticles.

In an embodiment the W nanoparticles are completely enclosed within a pore included in the strut.

Example 6a includes the system of example 5a, wherein the at least one of the W nanoparticles includes an aggregation of two or more W nanoparticles.

Example 7a includes the system of example 4a, wherein: the struts include a first strut that has a longitudinal axis that generally defines a length of the first strut and a horizontal axis that generally defines a width of the first strut;
the horizontal cross section through the first strut, intersecting the vertical and horizontal axes, intersects at least one the W nanoparticles and a portion of the polymer; and
the majority of the cross section includes the polymer and not the at least one of the W nanoparticles.

Example 8a includes the system of example 4a, wherein the foam comprises at least one isocyanate composition and at least one hydroxyl composition.

Example 9a includes the system of example 8a, wherein the at least one isocyanate composition is selected from the group consisting of: 1,6-hexamethylene diisocyante (HDI), (2,2,4 and 2,4,4) trimethyl-1,6-hexamethylene diisocyante (TMHDI), methylene diphenyl diisocyanate (MDI), toluene diisocyanate (TDI), and isophorone diisocyanate (IPDI).

Example 10a includes the system of example 8a, wherein the hydroxyl composition is selected from the group consisting of N,N,N',N'-Tetrakis(2-hydroxypropyl) ethylenediamine (HPED) and triethanolamine (TEA).

Example 11a includes the system of example 10a, wherein the polymer of the foam has increased toughness, increased density, smaller pore size, and increased wet and dry glass transition temperatures as compared to an additional foam that is identical to the foam except for having less than 4% W nanoparticles by volume.

Example 12a includes the system of example 10a, wherein the foam has a density of at least 0.040 g·cm-3, a porosity greater than 96%, a wet glass transition temperature of at least 38 degrees C., a toughness of at least 20 J·m-3, and a tensile strength of at least 60 kPa.

Another version of Example 12a includes the system of example 10a, wherein the foam has a density of at least 0.040 g·cm-3, a porosity greater than 96%, a wet glass transition temperature of at least 38 degrees C., a toughness of at least 20 J·m-3, a tensile strength of at least 60 kPa, pores no greater than 1 mm in diameter along a major axis of the pore, and pores with an aspect ratio no greater than 1.2.

Example 13a includes a method of manufacturing a radiopaque shape memory foam composition, the method comprising the steps of:
synthesizing an isocyanate premix;
curing the isocyanate premix;
synthesizing a hydroxyl premix;
mixing nanoparticles of radiopaque material with the cured isocyanate premix and one or more surfactants;
cooling the nanoparticle/isocyanate mixture to room temperature;
adding the hydroxyl premix to the cooled nanoparticle/isocyanate mixture;
adding a blowing agent to the nanoparticle/isocyanate/hydroxyl mixture and preparing a homogenous composition; and
heating the homogenous composition under vacuum conditions.

Example 14a includes the method of example 13a, wherein the isocyanate premix comprises a racemic mixture of (2,2,4 and 2,4,4) trimethyl-1,6-hexamethylene diisocyante (TMHDI) and hydroxyl groups containing triethanolamine (TEA) and N,N,N',N'-Tetrakis(2-hydroxypropyl) ethylenediamine (HPED).

Example 15a includes the method of example 13a, wherein the hydroxyl premix comprises hydroxyl groups containing TEA and HPED.

Example 16a includes the method of example 13a, wherein the radiopaque material is selected from the group consisting of tungsten, tungsten carbide, tungsten oxide, tantalum, gold, palladium, platinum, barium sulfate, zirconium, and aluminum oxide.

Example 17a includes the method of example 13a, wherein the blowing agent includes HFC-245fa,1,1,1,3,3-pentafluoropropane.

Example 18a includes the method of example 13a, wherein the homogenous composition is heated at 90° C., for 10 minutes at a vacuum of −10 cm Hg.

Example 19a includes a system comprising:
a neurovascular implant including a longitudinal axis and a maximum outer diameter, taken orthogonal to the longitudinal axis, no greater than 0.035 inches;
wherein (a) the implant includes a shape memory polymer foam comprising cells formed by struts, (b) the struts each include radiopaque nanoparticles having a maximum diameter that is less than 500 nm; and (d) the foam is crimped around a backbone.

Example 20a includes the system of example 19a, wherein:
the nanoparticles include at least one member selected from the group consisting of: tungsten carbide, tungsten oxide, silicate, tantalum, gold, palladium, platinum, barium sulfate, zirconium, and aluminum oxide; and
the foam comprises a mixture of one or more polyols.

Those having skill in the art, with the knowledge gained from the present disclosure, will recognize that various changes could be made to the methods disclosed herein without departing from the scope of the present invention. Mechanisms used to explain theoretical or observed phenomena or results, shall be interpreted as illustrative only and not limiting in any way the scope of the appended claims.

What is claimed is:

1. A system comprising:
a neurovascular implant including a longitudinal axis and a maximum outer diameter taken orthogonal to the longitudinal axis;
wherein (a) the implant includes a shape memory polymer foam comprising cells formed by struts, (b) the struts each include tungsten (W) nanoparticles having a maximum diameter that is less than 70 nm, (d) the foam is crimped around a backbone, and (e) the maximum outer diameter of the implant, when the foam is crimped, is no greater than 0.035 inches.

2. The system of claim 1, wherein foam includes at least 6% W nanoparticles by volume and no more than 10% W nanoparticles by volume.

3. The system of claim 2, wherein the foam, which is crimped around the backbone, has an X-ray density (X.D.) of at least 1.0 Hounsfield units (HU) when imaged at 45 KV.

4. The system of claim 2, wherein the foam includes a polymer, the polymer including at least one of polyurethane, polynorbornene, polymethylmethacrylate, poly(vinyl chloride), polyethylene, polyisoprene, styrene-butadiene copolymer, or combinations thereof.

5. The system of claim 4, wherein:
the struts include a first strut that has a longitudinal axis that generally defines a length of the first strut and a horizontal axis that generally defines a width of the first strut;
the horizontal axis intersects at least one of the W nanoparticles and a portion of the polymer; and
the majority of the width of the first strut includes the polymer and not the at least one of the W nanoparticles.

6. The system of claim 5, wherein the at least one of the W nanoparticles includes an aggregation of two or more W nanoparticles.

7. The system of claim 4, wherein:
the struts include a first strut that has a longitudinal axis that generally defines a length of the first strut and a horizontal axis that generally defines a width of the first strut;
the horizontal cross section through the first strut, intersecting the vertical and horizontal axes, intersects at least one of the W nanoparticles and a portion of the polymer; and
the majority of the cross section includes the polymer and not the at least one of the W nanoparticles.

8. The system of claim 4, wherein the foam comprises at least one isocyanate composition and at least one hydroxyl composition.

9. The system of claim 8, wherein the at least one isocyanate composition includes at least one of 1, 6-hexamethylene diisocyante (HDI), (2,2,4 and 2,4,4) trimethyl-1,6-hexamethylene diisocyante (TMHDI), methylene diphenyl diisocyanate (MDI), toluene diisocyanate (TDI), isophorone diisocyanate (IPDI), or combinations thereof.

10. The system of claim 8, wherein the hydroxyl composition includes at least one of N,N,N',N'-Tetrakis(2-hydroxypropyl) ethylenediamine (HPED), triethanolamine (TEA), or combinations thereof.

11. The system of claim 10, wherein the polymer of the foam has increased toughness, increased density, smaller pore size, and increased wet and dry glass transition temperatures as compared to an additional foam that is identical to the foam except for having less than 4% W nanoparticles by volume.

12. The system of claim 10, wherein the foam has a density of at least 0.040 g·cm$^{-3}$, a porosity greater than 96%, a wet glass transition temperature of at least 38 degrees C., a toughness of at least 20 J·m$^{-3}$, a tensile strength of at least 60 kPa, pores no greater than 1 mm in diameter along a major axis of the pore, and pores with an aspect ratio no greater than 1.2.

13. A system comprising:
a neurovascular implant including a longitudinal axis and a maximum outer diameter, taken orthogonal to the longitudinal axis, no greater than 0.035 inches;
wherein (a) the implant includes a shape memory polymer foam comprising cells formed by struts, (b) the struts each include radiopaque nanoparticles having a maximum diameter that is less than 500 nm; and (d) the foam is crimped around a backbone.

14. The system of claim 13, wherein:
the nanoparticles include at least one of: tungsten carbide, tungsten oxide, silicate, tantalum, gold, palladium, platinum, barium sulfate, zirconium, aluminum oxide, or combinations thereof; and
the foam comprises a mixture of one or more polyols.

* * * * *